(12) United States Patent
Osaki et al.

(10) Patent No.: US 7,160,936 B2
(45) Date of Patent: Jan. 9, 2007

(54) METHOD OF PRODUCING ULTRAVIOLET RADIATION ABSORBENT

(75) Inventors: Tatsuhiko Osaki, Gamagori (JP); Tetsuo Ichihashi, Sagamihara (JP)

(73) Assignees: Takemoto Yushi Kabushiki Kaisha, Aichi (JP); Teijin Dupont Films Japan Limited, Tokyo (JP)

( * ) Notice: Subject to any disclaimer, the term of this patent is extended or adjusted under 35 U.S.C. 154(b) by 0 days.

(21) Appl. No.: 11/100,193

(22) Filed: Apr. 5, 2005

(65) Prior Publication Data

US 2005/0202344 A1 Sep. 15, 2005

Related U.S. Application Data

(62) Division of application No. 10/882,463, filed on Jun. 30, 2004, now Pat. No. 6,908,998, which is a division of application No. 10/293,969, filed on Nov. 12, 2002, now Pat. No. 6,808,133.

(30) Foreign Application Priority Data

Nov. 20, 2001 (JP) .............. 2001-354368
Nov. 20, 2001 (JP) .............. 2001-354379
Nov. 20, 2001 (JP) .............. 2001-354404

(51) Int. Cl.
*C08K 5/34* (2006.01)
*C08K 5/48* (2006.01)
*C07D 265/32* (2006.01)
*C07D 265/12* (2006.01)
*C07D 498/00* (2006.01)

(52) U.S. Cl. .............. 524/87; 524/90; 544/73; 544/89

(58) Field of Classification Search .............. None
See application file for complete search history.

(56) References Cited

U.S. PATENT DOCUMENTS

| 3,989,698 | A | 11/1976 | Jacobs et al. .............. 260/244 |
| 4,446,262 | A | 5/1984 | Okumura et al. .............. 524/89 |
| 5,560,852 | A | 10/1996 | Mura .............. 424/402 |
| 2003/0096889 | A1 | 5/2003 | Sarkar |
| 2003/0130383 | A1 | 7/2003 | Osaki et al. |

FOREIGN PATENT DOCUMENTS

| JP | 61-291575 | 12/1986 |
| JP | 2000264879 | 9/2000 |

OTHER PUBLICATIONS

Hawley's Condensed Chemical Dictionary, 13th ed., © 1997 by Van Nostrand Reinhold, p. 33.*
The Merck Index, 13th ed., © 2001 by Merck & Co., Inc., p. 8056.*
Hamad et al., *Synthesis and reactions of 2,2'-(1,4-phenylene)-di-4H-benz-3, 1-oxazin-4-one*, Afinidat, vol. 55(475), pp. 225-228 (1998). CAS Online Abstract.
Bain and Smalley, *Synthesis of 2-Substituted-4H-3, 1-benzoxazin-4-ones*, J. Chem. Soc., Section C: Organic, vol. 13, pp. 1593-1597 (1968).

* cited by examiner

*Primary Examiner*—Zachary C. Tucker
(74) *Attorney, Agent, or Firm*—Beyer Weaver & Thomas LLP

(57) ABSTRACT

An ultraviolet radiation absorbent for thermoplastic polymer materials such as polyethylene terephthalate or polycarbonate contains cyclic imino ester compound of a specified structure in an amount of over 99.5 weight % and less than 100 weight % and having an acid value in the range of $1 \times 10^{-3}$–1 and/or a chlorine ion content in the range of $1 \times 10^{-1}$–$1 \times 10^3$ ppm.

2 Claims, No Drawings

METHOD OF PRODUCING ULTRAVIOLET RADIATION ABSORBENT

This is a divisional of application Ser. No. 10/882,463 filed Jun. 30, 2004 now U.S. Pat. No. 6,908,998, which is and is a divisional of application Ser. No. 10/293,969 filed Nov. 12, 2002, now U.S. Pat. No. 6,809,133 issued Oct. 26, 2004.

BACKGROUND OF THE INVENTION

This invention relates to methods of producing ultraviolet radiation absorbents for thermoplastic polymers. Films and various kinds of molded products such as boxes made of thermoplastic polymer materials undergo quality degradation such as discoloration and fading when exposed to ultraviolet radiation. Different kinds of ultraviolet radiation absorbents have therefore been in use for preventing such quality degradation for thermoplastic polymers as well as products made from them. The present invention relates to improvement in such ultraviolet radiation absorbents and methods of producing such improved absorbents.

Benzophenone compounds, benzotriazole compounds and salicylic acid compounds have been generally used as an ultraviolet radiation absorbent for thermoplastic polymers but it has been a problem that these absorbents are usually low in resistance against heat. In view of this problem, cyclic imino ester compounds have been proposed as ultraviolet radiation absorbents with improved heat resistance (U.S. Pat. No. 4,446,262, Japanese Patent Publications Tokko 62-5944 and 62-31027). These absorbents are themselves more resistant against heat but still have the problem that, when they are added or mixed to a thermoplastic polymer material such as polyethylene terephthalate or polycarbonate, they tend to adversely affect the original material characteristics of these thermoplastic polymers such as transparency. They also have the problem of sublimating and adversely affecting the workability and the environmental conditions during the mixing and molding processes when used for such thermoplastic polymer materials having high mixing and molding temperatures. There is also the problem that they do not store well although they may have to be stored for an extended period of time until they finally come to be used.

SUMMARY OF THE INVENTION

It is therefore an object of this invention to provide methods of producing improved ultraviolet radiation absorbents which are themselves highly resistant against heat, capable of producing products having the original material characteristics of thermoplastic polymers such as transparency when added and mixed with them without adversely affecting the workability or the environmental conditions and capable of being stored for an extended period of time.

The invention is based on the discovery by the present inventors as a result of their diligent investigations that absorbents containing cyclic imino ester compounds of a specified type in a specified amount and prepared with the acid value and/or the chlorine ion content maintained within a specified range satisfy the aforementioned and other objects.

DETAILED DESCRIPTION OF THE INVENTION

The invention relates to an ultraviolet radiation absorbent for thermoplastic polymer materials containing cyclic imino ester compound shown by Formula 1 given below in an amount of over 99.5 weight % and less than 100 weight % and prepared such that the acid value is in the range of $1 \times 10^{-3}$–1 or the chlorine ion content is in the range of $1 \times 10^{-1}$–$1 \times 10^{3}$ ppm, where Formula 1

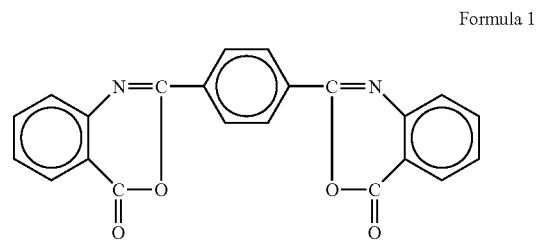

The invention also relates to a method of producing an ultraviolet radiation absorbent comprising Steps A, B and C, Step A being a process of separating a solid component containing N,N-bis(o-carboxyphenylterephthalamid) generated by amidation of anthranilic acid and terephthaloyl dichloride in the presence of a solvent and an alkali, Step B being a process of separating a solid component containing cyclic imino ester shown by Formula 1 generated by iminoesterification of N,N-bis(o-carboxyphenylterephthalamid) within the solid component separated in Step A and acetic anhydride in the presence of a solvent, and Step C being a process of processing the solid component separated in Step B with an alkaline solution and further washing with water to obtain an ultraviolet radiation absorbent for thermoplastic polymers containing cyclic imino ester compound shown by Formula 1 in an amount of over 99.5 weight % and less than 100 weight % t and prepared such that the acid value is in the range of $1 \times 10^{-3}$–1 or the chlorine ion content is in the range of $1 \times 10^{-1}$–$1 \times 10^{3}$ ppm.

The invention further relates to a method of producing an ultraviolet radiation absorbent comprising Steps a and b, Step a being a process of separating a solid component cyclic imino ester compound shown by Formula 1 generated by iminoesterification of isatoic anhydride and terephthaloyl dichloride in the presence of a solvent and an alkali, and Step b being a process of processing the solid component separated in Step a with an alkaline solution and further washing with water to obtain an ultraviolet radiation absorbent for thermoplastic polymers containing cyclic imino ester compound shown by Formula 1 in an amount of over 99.5 weight % and less than 100 weight % and prepared such that the acid value is in the range of $1 \times 10^{-3}$–1 or the chlorine ion content is in the range of $1 \times 10^{-1}$–$1 \times 10^{3}$ ppm.

In the subsequent description of the invention more in detail, the content of cyclic imino ester compound shown by Formula 1 is the value obtained by high performance liquid chromatography, the acid value is the value as measured according to JIS-K0070 and the chlorine ion content is the value measured by the mercury thiocyanate coloring method.

Ultraviolet radiation absorbents of this invention are not limited by the method of preparation. They may be prepared by (1) the method of adjusting the content of cyclic imino ester compound shown by Formula 1 and the acid value and/or the chlorine ion content of the product to be within the specified range in the process of producing cyclic imino ester compound shown by Formula 1 (hereinafter simply referred to as "cyclic imino ester") as it is being produced, or (2) the method of adjusting the content of cyclic imino ester and the acid value and/or the chlorine ion content by adding an organic acid such as terephthalic acid, isophthalic acid, anthranilic acid and isatoic acid as an acidic substance and/or an inorganic salt containing chlorine atom such as sodium chloride, potassium chloride and calcium chloride as a chlorine ion forming compound to the produced substantially pure cyclic imino ester such that the content of cyclic imino ester, the acid value and/or the chlorine ion content will be adjusted to be within the specified ranges. Of these two, however, the first is preferable from the point of view of cost of production. When the first method is used to adjust the content of cyclic imino ester and the acid value and/or the chlorine ion content of the product, this method of adjustment is not intended to limit the scope of the invention, but the aforementioned methods through Steps A, B and C and through Steps a and b are preferable.

The method through Steps A, B and C is explained first. Step A is a process of amidation of anthranilic acid and terephthaloyl dichloride in the presence of a solvent and an alkali and separating a solid component containing N,N'-bis(o-carboxyphenylterephthalamid). There is no particular limitation as to the ratio between anthranilic acid and terephthaloyl dichloride used for the amidation process but it is preferable to use 0.49–0.51 moles, and more preferably 0.5 moles, of terephthaloyl dichloride per one mole of anthranilic acid. Neither is there any particular limitation regarding the solvent but acetone, methylethyl ketone, water and their mixtures are preferred as the solvent for anthranilic acid. As for terephthaloyl dichloride, a non-protonic solvent such as acetone and xylene is preferable. Examples of alkali include (1) hydroxides of alkali metals such as sodium hydroxide and potassium hydroxide, (2) carbonates of alkali metals such as sodium carbonate and potassium carbonate, (3) hydrogencarbonates of alkali metals such as sodium hydrogencarbonate and potassium hydrogencarbonate and (4) organic alkalis such as pyridine, but a choice should be made depending on the solvent to be used such that it will be dissolved in the solvent. The amount of the alkali to be used must be sufficient for completely neutralizing the hydrochloric acid produced as by-product in the amidation reaction. The reaction temperature should preferably be 10–80° C. and more preferably 20–50° C. The method of adding a solution of terephthaloyl dichloride to a liquid mixture or slurry of anthranilic acid and an alkali for the amidation is preferable.

In Step A, N,N'-bis(o-carboxyphenylterephthalamid) is obtained by an amidation reaction of anthranilic acid and terephthaloyl dichloride. The reaction system containing N,N'-bis(o-carboxyphenylterephthalamid) thus produced may be in the form of a slurry or a solution, depending on the kind of the solvent and the alkali which are used. If it is in the form of a slurry, a solid component containing N,N'-bis(o-carboxyphenylterephthalamid) is separated by filtering or centrifugation. If it is in the form of a solution, a solid component containing N,N'-bis(o-carboxyphenyl-terephthalamid) is separated by distilling away the solvent. The solid component thus separated may be directly used in Step B or may be washed with water for removing the by-product salts to a certain extent and then dried to be used in Step B.

The solid component separated in Step A is used in Step B for an iminoesterification reaction between N,N'-bis(o-carboxyphenylterephthalamid) in the solid component and acetic anhydride in the presence of a solvent to separate a solid component containing cyclic imino ester. The ratio of N,N'-bis(o-carboxyphenylterephthalamid) in the solid component and acetic anhydride used for the iminoesterification is usually 4–20 moles, and preferably 5–10 moles, of acetic acid per one mole of N,N'-bis(o-carboxyphenylterephthalamid). There is no particular limitation regarding the solvent but aromatic hydrocarbons such as toluene and xylene are preferable. The reaction temperature is preferably 100–180° C. and more preferably 110–140° C. As for the method of the reaction, it is preferable to carry out the iminoesterification with reflux by adding acetic anhydride and the solvent to the solid component separated in Step A.

In Step B, cyclic imino ester is generated by the iminoesterification reaction between N,N'-bis(o-carboxyphenyl-terephthalamid) and acetic anhydride. The reaction system containing cyclic imino ester thus generated is in the form of a slurry. In Step B, a solid component containing cyclic imino ester is separated from such a slurry by filtering or centrifugation.

In Step C, the solid component separated in Step B containing cyclic imino ester is processed with an alkaline solution and washed with water to obtain an ultraviolet radiation absorbent comprising a product prepared so as to contain cyclic imino ester in an amount of over 99.5 weight % and less than 100 weight % and to have its acid value within the range of $1 \times 10^{-3}$–1 and/or its chlorine ion content within the range of $1 \times 10^{-1}$–$1 \times 10^3$ ppm.

The method of adjusting the content of cyclic imino ester and the acid value of the solid component containing cyclic imino ester in Step C by an alkali treatment and containing cyclic imino ester separated in Step B by using a filter such as a Nutsche filter, an Oliver vacuum filter or a filter press or a centrifuge such as a basket type centrifuge or a centrifugal decanter is preliminarily measured. Thereafter, water, acetone or an aqueous organic solvent such as methanol or a mixture thereof is added to this solid component such that the concentration of the solid component will be 20–30 weight % to make a slurry. Thereafter, an alkali is added such that the acid value will change from the originally measured value to a resultant value in the range of $1 \times 10^3$–1 and an alkali treatment is effected at 10–40° C. for 1–2 hours with stirring. Next, after the solid component containing cyclic imino ester is separated from the alkali-treated slurry, the separated solid component is washed with water.

There is no particular limitation as to the kind of alkali to be used for this alkali treatment. Examples of alkali which may be used for this purpose include (1) alkoxides of alkali metals such as sodium methoxide, sodium ethoxide and potassium methoxide, (2) hydroxides of alkali metals such as sodium hydroxide and potassium hydroxide, (3) carbonates of alkali metals such as sodium carbonate and potassium carbonate, (4) hydrogencarbonates of alkali metals such as sodium hydrogencarbonate and potassium hydrogencarbonate, (5) ammonia water and (6) lower alkyl quaternary ammonium hydroxides such as tetramethylammonium hydroxide and tetraethylammonium hydroxide. Of these, inorganic salts of alkali metals such as sodium hydroxide and sodium carbonate are preferable.

Neither is there any particular limitation as to the process of washing with water. As to the quantity of water to be used, it is preferable to use about 3–20 times the weight of the solid component and more preferably about 5–10 times. The water temperature should be preferably 20–80° C.

After the solid component containing cyclic imino ester is treated with an alkali and washed with water, it is separated and dried, and its content of cyclic imino ester and acid value are measured in order to ascertain that they are within the desired ranges. If the measurements show that the content of cyclic imino ester is too low or that the acid value is too high, the aforementioned alkali treatment and the process of washing with water are repeated.

The method of adjusting the content of cyclic imino ester and the chlorine ion content of the solid component containing cyclic imino ester in Step C by an alkali treatment and washing with water will be explained next. First, a slurry is prepared by adding water, acetone, an aqueous solvent such as methanol or their mixture to the solid component containing cyclic imino ester separated as explained above in Step B such that the concentration of the solid component becomes 20–30 weight %. An appropriate amount of alkali is added to this slurry in order to make it easier to remove chlorine ion and an alkali treatment is effected at 10–40° C. for 1–2 hours with stirring. After the solid component containing cyclic imino ester is separated from the slurry which has undergone this alkali treatment, it is washed with water. The kind of alkali to be used and the conditions for the washing process with water are as explained above.

After the solid component containing cyclic imino ester is treated with an alkali and washed with water as explained above, it is separated and dried, and the content of cyclic imino ester and the chlorine ion content are measured in order to ascertain that they are within the desired ranges. If the measurement shows that the content of cyclic imino ester is too low or that the chlorine ion content is too high, the aforementioned alkali treatment and the process of washing with water are repeated.

The method of adjusting the content of cyclic imino ester, the acid value and the chlorine ion content of the solid component containing cyclic imino ester in Step C by an alkali treatment and washing with water will be explained next. First, the acid value of the solid component containing cyclic imino ester separated in Step B as explained above is measured preliminarily. After a solvent for dissolving the alkali to be added such as water, acetone, an aqueous solvent such as methanol or their mixture is added to make a slurry with the concentration of the solid component equal to 20–30 weight %, the alkali is added such that the acid value will change from the preliminarily measured value to a value within the range of $1\times10^{-3}$–1 after the alkali treatment at 10–40° C. for 1–2 hours with stirring. The solid component containing cyclic imino ester is separated from the slurry which has undergone the alkali treatment and the separated solid component is washed with water such that its chlorine ion content comes to be within the range of $1\times10^{-1}$–$1\times10^{3}$ ppm. The alkali treatment as explained above on the solid component containing cyclic imino ester is not only for the purpose of adjusting the content of cyclic imino ester and the acid value but is also important because it makes it easier to remove the chlorine ions after the washing process with water to be carried out subsequently. The kind of alkali to be used and the conditions for the washing process with water are as explained above.

After the solid component containing cyclic imino ester is treated with an alkali and washed with water as explained above, it is separated and dried, and its content of cyclic imino ester, acid value and chlorine ion content are measured in order to ascertain that they are within the desired ranges. If the measurements show that the content of cyclic imino ester is too low or the acid value and the chlorine ion content are too high, the aforementioned alkali treatment and the process of washing with water are repeated.

After Steps A, B and C are carried out as explained above, an ultraviolet radiation absorbent comprising a product which contains cyclic imino ester in an amount of over 99.5 weight % and less than 100 weight % and is adjusted to have its acid value with the range $1\times10^{-3}$–1 and/or its chlorine ion content within the range of $1\times10^{-1}$–$1\times10^{3}$ is obtained. In Step C, however, it is preferable to obtain a product containing cyclic imino ester in an amount of over 99.9 weight % and less than 100 weight % and having its acid value adjusted to $3\times10^{-3}$–$1\times10^{-1}$ or its chlorine ion content to $1.5\times10^{-1}$–$5\times10^{2}$ ppm, and is even more preferable to obtain a product containing cyclic imino ester in an amount of over 99.9 weight % and less than 100 weight % and having both its acid value adjusted to $3\times10^{-3}$–$1\times10^{-1}$ and its chlorine ion content to $1.5\times10^{-1}$–$5\times10^{2}$ ppm Next, the method through Steps a and b is explained. Step a is a process of separating a solid component containing cyclic imino ester generated by iminoesterification of isatoic anhydride and terephthaloyl dichloride in the presence of a solvent and an alkali. There is no particular limitation as to the ratio between isatoic anhydride and terephthaloyl dichloride used for the iminoesterification but it is preferable to use 0.95–1.05 moles of terephthaloyl dichloride per 2 moles of isatoic anhydride. Neither is there any particular limitation regarding the solvent. Non-protonic solvents containing nitrogen such as dimethyl formaldehyde and dimethyl acetoamide, ketone solvents such as acetone and methylethyl ketone, ether solvents such as tetrahydrofuran and dioxane, and their mixtures are examples that may be used but acetone is preferred. Neither is there any particular limitation regarding the alkali. Examples include (1) hydroxides of alkali metals such as sodium hydroxide and potassium hydroxide, (2) lower alkyl quaternary ammonium hydroxides such as tetramethylammonium hydroxide and tetraethylammonium hydroxide and (3) organic alkalis such as pyridine, but pyridine is preferred. An appropriate kind of alkali should be used, depending on the selected kind of solvent, so as to be dissolved in the selected kind of solvent. The amount of the alkali to be used is preferably selected such that the hydrochloric acid generated as by-product in the iminoesterification will be 100% neutralized. The reaction temperature should preferably be 10–80° C. and more preferably 20–50° C. As for the method of the reaction, it is preferable to add a solution of terephthaloyl dichloride to a mixed solution or slurry of isatoic anhydride for iminoesterification.

In Step a, cyclic imino ester is generated by iminoesterification of isatoic anhydride and terephthaloyl dichloride. The reaction system containing cyclic imino ester thus generated is either in the form or a slurry or in the form of a solution, depending on the kinds of the solvent and the alkali which have been used. If it is in the form of a slurry, the solid component containing cyclic imino ester is separated by filtering or by centrifugation. If it is in the form of a solution, the solvent is distilled away to separate the solid component containing cyclic imino ester. The solid component thus separated may be directly used in Step b or may be washed with water in order to remove by-product salts to a certain extent and dried before being used in Step b.

In Step b, the solid component containing cyclic imino ester separated in Step a is treated with an alkali and then washed with water to obtain an ultraviolet radiation absorbent comprising a product containing cyclic imino ester in an amount of over 99.5 weight % and less than 100 weight % and prepared such that its acid value is in the range of $1\times10^{-3}$–1 and/or that its chlorine ion content is in the range of $1\times10^{-1}$–$1\times10^{3}$ ppm. Thus, Step b is the same as aforementioned Step C.

In this manner, an ultraviolet radiation absorbent, comprising a product containing cyclic imino ester in an amount of over 99.5 weight % and less than 100 weight % and prepared such that its acid value is in the range of $1\times10^{-3}$–1 and/or that its chlorine ion content is in the range of $1\times10^{-1}$–$1\times10^{3}$ ppm, is obtained through Steps a and b. In Step b, however, it is preferable to obtain a product containing cyclic imino ester in an amount of over 99.9 weight % and less than 100 weight % and having an acid value of $3\times10^{-3}$–$1\times10^{-1}$ or a chlorine ion content of $1.5\times10^{-1}$–$5\times10^{2}$ ppm, and it is even more preferable to obtain a product containing cyclic imino ester by over 99.9 weight % and less than 100 weight % and having both an acid value of $3\times10^{-3}$–$1\times10^{-1}$ and a chlorine ion content of $1.5\times10^{-1}$–$5\times10^{2}$ ppm.

The invention does not place any particular limitation on the kind of thermoplastic polymers to which ultraviolet radiation absorbents as described above should be applied. Examples of thermoplastic polymers to which they may be applied include (1) thermoplastic polyesters such as polyethylene terephthalate, polyethylene naphthalate and polybutylene terephthalate, (2) polycarbonates, (3) styrene polymers such as polystyrene, styrene-acrylonitrile-butadien copolymers and high-impact polystyrene, (4) acryl polymers, (5) amid polymers, (6) polyphenylene ether, (7) polyolefins such as polyethylene, polypropylene and vinyl polychloride, (8) polyoxymethylene, (9) polyphenylene sulfide, (10) lactic acid polymers and (11) mixtures of these thermoplastic polymers. Absorbents according to this invention are particularly effective when added to and mixed with polyethylene terephthalate and polycarbonates which have high transparency and require a high mixing temperature and a high molding temperature.

Ultraviolet radiation absorbents for thermoplastic polymers embodying this invention, having the content of cyclic imino ester and acid value and/or chlorine ion content adjusted within a specified range, are themselves highly resistant against heat and can be added to and mixed with thermoplastic polymers such as polyethylene terephthalate and polycarbonates requiring a high mixing temperature and a high molding temperature to produce molded products having the same high transparency originally possessed by these thermoplastic polymers. Those having the acid value adjusted to a specified range, in particular, do not adversely affect the workability or the environmental condition in the mixing and molding processes even when added to and mixed with thermoplastic polymers such as polyethylene terephthalate and polycarbonates requiring a high mixing temperature and a high molding temperature. Those having the chlorine ion content adjusted to within a specified range store well. Those having the acid value adjusted to within a specified range and the chlorine ion content adjusted to within a specified range do not adversely affect the workability or the environmental condition in the mixing and molding processes even when added to and mixed with thermoplastic polymers such as polyethylene terephthalate and polycarbonates having a high mixing temperature and a high molding temperature and also store well.

The invention does not particularly limit the amount of the absorbent to be used. When it is applied to thermoplastic polymers, the ratio is usually 0.1–5 weight parts to 100 weight parts of thermoplastic polymers.

The invention is described next with reference to the following twelve embodiments.

(1) Ultraviolet radiation absorbent containing cyclic imino ester by 99.99 weight % and having acid value adjusted to $1.5\times10^{-3}$.

(2) Ultraviolet radiation absorbent containing cyclic imino ester by 99.99 weight % and having acid value adjusted to $4\times10^{-3}$.

(3) Ultraviolet radiation absorbent containing cyclic imino ester by 99.95 weight % and having acid value adjusted to $8\times10^{-2}$.

(4) Ultraviolet radiation absorbent containing cyclic imino ester by 99.65 weight % and having acid value adjusted to $9\times10^{-1}$.

(5) Ultraviolet radiation absorbent containing cyclic imino ester by 99.99 weight % and having chlorine ion content adjusted to $1.5\times10^{-1}$ ppm.

(6) Ultraviolet radiation absorbent containing cyclic imino ester by 99.99 weight % and having chlorine ion content adjusted to $2\times10^{-1}$ ppm.

(7) Ultraviolet radiation absorbent containing cyclic imino ester by 99.90 weight % and having chlorine ion content adjusted to $4\times10^{2}$ ppm.

(8) Ultraviolet radiation absorbent containing cyclic imino ester by 99.94 weight % and having chlorine ion content adjusted to $9.5\times10^{2}$ ppm.

(9) Ultraviolet radiation absorbent containing cyclic imino ester by 99.96 weight % and having acid value adjusted to $3\times10^{-3}$ and chlorine ion content adjusted to $1.5\times10^{-1}$ ppm.

(10) Ultraviolet radiation absorbent containing cyclic imino ester by 99.94 weight % and having acid value adjusted to $5\times10^{3}$ and chlorine ion content adjusted to $3\times10^{-1}$ ppm.

(11) Ultraviolet radiation absorbent containing cyclic imino ester by 99.92 weight % and having acid value adjusted to $9\times10^{-2}$ and chlorine ion content adjusted to $3\times10^{2}$ ppm.

(12) Ultraviolet radiation absorbent containing cyclic imino ester by 99.71 weight % and having acid value adjusted to $8\times10^{-1}$ and chlorine ion content adjusted to $9\times10^{2}$ ppm.

The invention is described next by way of examples but it goes without saying that these examples are not intended to limit the scope of the invention. In what follows, "part" will mean "weight part" and "%" will mean "weight %".

Part 1 (Preparation of Ultraviolet Radiation Absorbents for Thermoplastic Polymers: No. 1)

TEST EXAMPLE 1

Anthranilic acid 13.7 g (0.1 moles), anhydrous sodium carbonate 5.19 g (0.049 moles) and water 100 ml were placed in a flask with four openings provided with a thermometer, a stirrer, a reflux cooler and a dropper funnel and the mixture was dissolved with stirring for 10 minutes. After a solution obtained by dissolving terephthaloyl dichloride 10.2 g (0.05 moles) in acetone 300 ml was dropped into this flask by means of the dropper funnel over one hour at room temperature, a slurry with solid component containing N,N'-bis(o-carboxyphenylterephthalamid) was obtained by amidation for one hour with reflux. A solid component was separated from this slurry and after it was washed with water 300 ml and dried, a dried solid component 19.9 g was obtained. The dried solid component 19.9 g, acetic anhydride 102 g (1 mole) and toluene 100 ml were placed in the flask with four openings for iminoesterification with reflux for 6 hours, and after it was cooled down to room temperature, the solid component was filtered out. After this filtered solid component was washed with acetone 100 ml and dried, a solid component 17.3 g (acid value 2.1) containing cyclic imino ester was obtained. Finally, this solid component 17 g and water 68 g were placed in the flask and 1% aqueous solution of sodium hydroxide 2.50 g was added with stirring and an alkali treatment was effected at 25° C. for 30 minutes with stirring. The alkali-treated solid component was filtered out and washed with warm water 160 g at 60° C. The washed solid component was dried for 2 hours with a hot-air drier at 100° C. to obtain yellowish powder 16.6 g. This yellowish powder was analyzed and found to contain cyclic imino ester by 99.99%, and its acid value was $1.5 \times 10^{-3}$. This will be referred to as Absorbent (P-1). The content of cyclic imino ester was measured by high performance liquid chromatography using chloroform as the elution liquid and a UV detector for detection.

TEST EXAMPLE 2

Anthranilic acid 13.7 g (0.1 moles), pyridine 7.74 g (0.098 moles) and acetone 200 ml were placed in a flask with four openings as in Test Example 1, and the mixture was dissolved with stirring for 10 minutes. After a solution obtained by dissolving terephthaloyl dichloride 10.2 g (0.05 moles) in acetone 100 ml was dropped into this flask by means of the dropper funnel over one hour at room temperature, a slurry with solid component containing N,N'-bis(o-carboxyphenylterephthalamid) was obtained by amidation for one hour with reflux. A solid component was separated from this slurry and after it was washed with water 300 ml and dried, a dried solid component 18.0 g was obtained. The dried solid component 18.0 g, acetic anhydride 102 g (1 mole) and toluene 100 ml were placed in the flask with four openings for iminoesterification with reflux for 6 hours, and after it was cooled down to room temperature, the solid component was filtered out. After this filtered solid component was washed with acetone 100 ml and dried, a solid component 15.0 g (acid value 1.3) containing cyclic imino ester was obtained. Finally, this solid component 14 g and methanol 68 g were placed in the flask and 1% solution of sodium methoxide methanol 1.71 g was added with stirring and an alkali treatment was effected at 25° C. for 30 minutes with stirring. The alkali-treated solid component was filtered out and washed with warm water 140 g at 40° C. The washed solid component was dried for 2 hours with a hot-air drier at 100° C. to obtain yellowish powder 13.5 g. This yellowish powder was analyzed and found to contain cyclic imino ester by 99.99%, and its acid value was $4 \times 10^{-3}$. This will be referred to as Absorbent (P-2).

TEST EXAMPLE 3

Isatoic anhydride 16.3 g (0.1 moles), pyridine 7.74 g (0.098 moles) and acetone 200 ml were placed in a flask with four openings as in Test Example 1, and the mixture was dissolved with stirring for 10 minutes. After a solution obtained by dissolving terephthaloyl dichloride 10.2 g (0.05 moles) in acetone 100 ml was dropped into this flask by means of the dropper funnel over one hour at room temperature, a slurry with solid component containing cyclic imino ester was obtained by iminoesterification for one hour with reflux. A solid component was separated from this slurry and after it was washed with water 300 ml and dried, a dried solid component 15.9 g (acid value 3.0) containing cyclic imino ester was obtained. The dried solid component 15 g and water 48 g were placed in the flask and 1% aqueous solution of sodium carbonate 4.16 g was added with stirring and an alkali treatment was effected at 30° C. for 30 minutes with stirring. The alkali-treated solid component was filtered out and washed with warm water 100 g at 60° C. The washed solid component was dried for 2 hours with a hot-air drier at 100° C. to obtain yellowish powder 14.5 g. This yellowish powder was analyzed and found to contain cyclic imino ester by 99.95%, and its acid value was $8 \times 10^{-2}$. This will be referred to as Absorbent (P-3).

TEST EXAMPLE 4

Anthranilic acid 13.7 g (0.1 moles), potassium hydroxide 5.32 g (0.095 moles) and water 100 ml were placed in a flask with four openings as in Test Example 1, and the mixture was dissolved with stirring for 10 minutes. After a solution obtained by dissolving terephthaloyl dichloride 10.2 g (0.05 moles) in acetone 200 ml was dropped into this flask by means of the dropper funnel over one hour at room temperature, a slurry with solid component containing N,N'-bis (o-carboxyphenylterephthalamid) was obtained by amidation for one hour with reflux. A solid component was separated from this slurry and after it was washed with water 300 ml and dried, a dried solid component 19.8 g was obtained. The dried solid component 19.8 g, acetic anhydride 102 g (1 mole) and toluene 100 ml were placed in the flask for iminoesterification with reflux for 6 hours, and after it was cooled down to room temperature, a solid component 15.5 g (acid value 5.1) containing cyclic imino ester was obtained. This dried solid component 15 g and water 35 g were placed in the flask and 1% aqueous solution of potassium hydroxide 7.50 g was added with stirring and an alkali treatment was effected at 25° C. for 30 minutes with stirring. The alkali-treated solid component was filtered out and washed with warm water 160 g at 60° C. The washed solid component was dried for 2 hours with a hot-air drier at 100° C. to obtain yellowish powder 14.2 g. This yellowish powder was analyzed and found to contain cyclic imino ester by 99.65%, and its acid value was $9 \times 10^{-1}$. This will be referred to as Absorbent (P-4).

COMPARISON EXAMPLE 1

Absorbent (P-1) obtained in Test Example 1 10 g and $1 \times 10^{-2}$% aqueous solution of sodium hydroxide 1000 ml were placed in a beaker. After it was stirred for one hour with a mixer, a solid component was filtered. The filtered solid component and water 1000 ml were placed in a beaker, and after it was stirred for one hour with a mixer, a solid component was filtered. This routine was repeated three times and the solid component thus obtained was dried for one hour at 100° C. to obtain yellowish powder. This yellowish powder was analyzed and found to contain cyclic imino ester by 100.00%, and its acid value was $6 \times 10^{-4}$. This will be referred to as Absorbent (R-1).

COMPARISON EXAMPLE 2

Yellowish powder 16.9 g was obtained in the same way as in Test Example 1 except that the alkali treatment was dispensed with. This yellowish powder was analyzed and found to contain cyclic imino ester by 99.41%, and its acid value was 1.3. This will be referred to as Absorbent (R-2).

Part 2 (Preparation of Ultraviolet Radiation Absorbents for Thermoplastic Polymers: No. 2)

TEST EXAMPLE 5

Anthranilic acid 13.7 g (0.1 moles), anhydrous sodium carbonate 5.19 g (0.049 moles) and water 100 ml were placed in a flask with four openings provided with a thermometer, a stirrer, a reflux cooler and a dropper funnel and the mixture was dissolved with stirring for 10 minutes. After a solution obtained by dissolving terephthaloyl dichloride 10.2 g (0.05 moles) in acetone 300 ml was dropped into this flask by means of the dropper funnel over one hour at room temperature, a slurry with solid component containing N,N'-bis(o-carboxyphenylterephthalamid) was obtained by amidation for one hour with reflux. A solid component was separated from this slurry and after it was washed with water 300 ml and dried, a dried solid component 19.7 g was obtained. The dried solid component 19.7 g, acetic anhydride 102 g (1 mole) and toluene 100 ml were placed in the flask with four openings for iminoesterification with reflux for 6 hours, and after it was cooled down to room temperature, the solid component was filtered out. After this filtered solid component was washed with acetone 100 ml and dried, a solid component 17.2 g containing cyclic imino ester was obtained. Finally, this solid component 17 g and water 68 g were placed in the flask and 1% aqueous solution of sodium hydroxide 2.42 g was added with stirring and an alkali treatment was effected at 25° C. for 30 minutes with stirring. The alkali-treated solid component was filtered out and washed with warm water 160 g at 60° C. The washed solid component was dried for 2 hours with a hot-air drier at 100° C. to obtain yellowish powder 16.7 g. This yellowish powder was analyzed and found to contain cyclic imino ester by 99.99%, and its chlorine ion content was $1.5 \times 10^{-1}$ ppm. This will be referred to as Absorbent (P-5).

The chlorine ion content was measured as follows by the mercury thiocyanate coloring method. Absorbent (P-5) 10 g is accurately measured and placed in a triangular flask together with ion exchange water 10 ml. An air cooler tube is attached to this flask and it is heated for one hour at 90° C. while shaking it from time to time. After it is cooled to the room temperature, a filtrate is obtained by filtering. The filtrate 10 ml is collected in a test tube, a nitric acid solution of ferric nitrate (obtained by dissolving 200 g of ferric nitrate in 500 ml of 5N nitric acid) 2 ml and a mercuric thiocyanate solution (obtained by dissolving 1 g of mercuric thiocyanate in 250 ml of methyl alcohol) are added and it is shaken together. Ten minutes after the addition of the mercuric thiocyanate solution, the absorbance at 460 nm is measured by means of a spectrophotometer. Separately, a calibration line is prepared by using a standard liquid of sodium chloride of the optical grade and the chlorine ion content of Absorbent (P-5) is obtained from this calibration line.

TEST EXAMPLE 6

Anthranilic acid 13.7 g (0.1 moles), pyridine 7.74 g (0.098 moles) and acetone 200 ml were placed in a flask with four openings as in Test Example 5, and the mixture was dissolved with stirring for 10 minutes. After a solution obtained by dissolving terephthaloyl dichloride 10.2 g (0.05 moles) in acetone 100 ml was dropped into this flask by means of the dropping funnel over one hour at room temperature, a slurry with solid component containing N,N'-bis(o-carboxyphenyl-terephthalamid) was obtained by amidation for one hour with reflux. A solid component was filtered out from this slurry and after it was washed with water 300 ml and dried, a dried solid component 17.8 g was obtained. The dried solid component 17.8 g, acetic anhydride 102 g (1 mole) and toluene 100 ml were placed in the flask with four openings for iminoesterification with reflux for 6 hours, and after it was cooled down to room temperature, the solid component was filtered out. After this filtered solid component was washed with acetone 100 ml and dried, a solid component 14.7 g containing cyclic imino ester was obtained. Finally, this solid component 14 g and methanol 68 g were placed in the flask and 1% solution of sodium methoxide methanol 1.71 g was added with stirring and an alkali treatment was effected at 25° C. for 30 minutes with stirring. The alkali-treated solid component was filtered out and washed with warm water 140 g at 40° C. The washed solid component was dried for 2 hours with a hot-air drier at 100° C. to obtain yellowish powder 13.6 g. This yellowish powder was analyzed and found to contain cyclic imino ester by 99.99%, and its chlorine ion content was $2 \times 10^{-1}$ ppm. This will be referred to as Absorbent (P-6).

TEST EXAMPLE 7

Isatoic anhydride 16.3 g (0.1 moles), pyridine 7.74 g (0.098 moles) and acetone 200 ml were placed in a flask with four openings as in Test Example 5, and the mixture was dissolved with stirring for 10 minutes. After a solution obtained by dissolving terephthaloyl dichloride 10.2 g (0.05 moles) in acetone 100 ml was dropped into this flask by means of the dropping funnel over one hour at room temperature, a slurry with solid component containing cyclic imino ester was obtained by iminoesterification for one hour with reflux. A solid component was separated from this slurry and after it was washed with water 300 ml and dried, a dried solid component 16.0 g containing cyclic imino ester was obtained. The dried solid component 15 g and water 48 g were placed in the flask and 1% aqueous solution of sodium carbonate 4.24 g was added with stirring and an alkali treatment was effected at 30° C. for 30 minutes with stirring. The alkali-treated solid component was filtered out and washed with warm water 100 g at 60° C. The washed solid component was dried for 2 hours with a hot-air drier at 100° C. to obtain yellowish powder 14.7 g. This yellowish powder was analyzed and found to contain cyclic imino ester by 99.90%, and its chlorine ion content was $4 \times 10^2$ ppm. This will be referred to as Absorbent (P-7).

TEST EXAMPLE 8

Anthranilic acid 13.7 g (0.1 moles), potassium hydroxide 5.32 g (0.095 moles) and water 100 ml were placed in a flask with four openings as in Test Example 5, and the mixture was dissolved with stirring for 10 minutes. After a solution obtained by dissolving terephthaloyl dichloride 10.2 g (0.05 moles) in acetone 200 ml was dropped into this flask by means of the dropper funnel over one hour at room temperature, a slurry with solid component containing N,N'-bis (o-carboxyphenylterephthalamid) was obtained by amidation for one hour with reflux. A solid component was separated from this slurry and after it was washed with water 300 ml and dried, a dried solid component 19.7 g was obtained. The dried solid component 19.7 g, acetic anhydride 102 g (1 mole) and toluene 100 ml were placed in the flask for iminoesterification with reflux for 6 hours, and after it was cooled down to room temperature, the solid component was filtered out. After this filtered solid component was washed with acetone 100 ml and dried, a solid component 15.3 g containing cyclic imino ester was obtained. This dried solid component 15 g and water 35 g were placed in the flask and 1% aqueous solution of potassium hydroxide 7.46 g was added with stirring and an alkali treatment was effected at 25° C. for 30 minutes with stirring. The alkali-treated solid component was filtered out and washed with warm water 160 g at 60° C. The washed solid component was dried for 2 hours with a hot-air drier at 100° C. to obtain yellowish powder 14.5 g. This yellowish powder was analyzed and found to contain cyclic imino ester by 99.94%, and its chlorine ion content was $9.5 \times 10^2$ ppm. This will be referred to as Absorbent (P-8).

COMPARISON EXAMPLE 3

Absorbent (P-5) obtained in Test Example 5 10 g and $1 \times 10^{-2}$% aqueous solution of sodium hydroxide 1000 ml were placed in a beaker. After it was stirred for one hour with a mixer, a solid component was filtered. The filtered solid component and water 1000 ml were placed in a beaker, and after it was stirred for one hour with a mixer, a solid component was filtered. This routine was repeated three times and the solid component thus obtained was dried for one hour at 100° C. to obtain yellowish powder. This yellowish powder was analyzed and found to contain cyclic imino ester by 100.00%, and its chlorine ion content was $5 \times 10^{-2}$ ppm. This will be referred to as Absorbent (R-3).

COMPARISON EXAMPLE 4

Yellowish powder 17.0 g was obtained in the same way as in Test Example 5 except that the alkali treatment was dispensed with. This yellowish powder was analyzed and found to contain cyclic imino ester by 98.79%, and its chlorine ion content was $2 \times 10^{-3}$ ppm. This will be referred to as Absorbent (R-4).

Part 3 (Preparation of Ultraviolet Radiation Absorbents for Thermoplastic Polymers: No. 3)

TEST EXAMPLE 9

Anthranilic acid 13.7 g (0.1 moles), anhydrous sodium carbonate 5.19 g (0.049 moles) and water 100 ml were placed in a flask with four openings provided with a thermometer, a stirrer, a reflux cooler and a dropper funnel and the mixture was dissolved with stirring for 10 minutes. After a solution obtained by dissolving terephthaloyl dichloride 10.2 g (0.05 moles) in acetone 300 ml was dropped into this flask by means of the dropper funnel over one hour at room temperature, a slurry with solid component containing N,N'-bis(o-carboxyphenylterephthalamid) was obtained by amidation for one hour with reflux. A solid component was separated from this slurry and after it was washed with water 300 ml and dried, a dried solid component 19.7 g was obtained. The dried solid component 19.7 g, acetic anhydride 102 g (1 mole) and toluene 100 ml were placed in the flask with four openings for iminoesterification with reflux for 6 hours, and after it was cooled down to room temperature, the solid component was filtered out. After this filtered solid component was washed with acetone 10 ml and dried, a solid component 17.4 g (acid value 2.3) containing cyclic imino ester was obtained. Finally, this solid component 17 g and water 68 g were placed in the flask and 1% aqueous solution of sodium hydroxide 2.79 g was added with stirring and an alkali treatment was effected at 25° C. for 30 minutes with stirring. The alkali-treated solid component was filtered out and washed with warm water 160 g at 60° C. After the washed solid component was dehydrated, it was dried for 2 hours with a hot-air drier at 100° C. to obtain yellowish powder 16.5 g. This yellowish powder was analyzed and found to contain cyclic imino ester by 99.96%. Its acid value was $3 \times 10^{-3}$ and its chlorine ion content was $1.5 \times 10^{-1}$ ppm. This will be referred to as Absorbent (P-9).

TEST EXAMPLE 10

Anthranilic acid 13.7 g (0.1 moles), pyridine 7.74 g (0.098 moles) and acetone 200 ml were placed in a flask with four openings as in Test Example 9, and the mixture was dissolved with stirring for 10 minutes. After a solution obtained by dissolving terephthaloyl dichloride 10.2 g (0.05 moles) in acetone 100 ml was dropped into this flask by means of the dropper funnel over one hour at room temperature, a slurry with solid component containing N,N'-bis(o-carboxyphenyl-terephthalamid) was obtained by amidation for one hour with reflux. A solid component was filtered out from this slurry and after it was washed with water 300 ml and dried, a dried solid component 17.9 g was obtained. The dried solid component 17.9 g, acetic anhydride 102 g (1 mole) and toluene 100 ml were placed in the flask with four openings for iminoesterification with reflux for 6 hours, and after it was cooled down to room temperature, the solid component was filtered out. After this filtered solid component was washed with acetone 100 ml and dried, a solid component 15.1 g (acid value 1.4) containing cyclic imino ester was obtained. Finally, this solid component 14 g and methanol 68 g were placed in the flask and 1% solution of sodium methoxide methanol 1.88 g was added with stirring and an alkali treatment was effected at 25° C. for 30 minutes with stirring. The alkali-treated solid component was filtered out and washed with warm water 140 g at 40° C. After the washed solid component was dehydrated, it was dried for 2 hours with a hot-air drier at 100° C. to obtain yellowish powder 13.5 g. This yellowish powder was analyzed and found to contain cyclic imino ester by 99.94%. Its acid value was $5 \times 10^{-3}$ and its chlorine ion content was $3 \times 10^{-1}$ ppm. This will be referred to as Absorbent (P-10).

TEST EXAMPLE 11

Isatoic anhydride 16.3 g (0.1 moles), pyridine 7.74 g (0.098 moles) and acetone 200 ml were placed in a flask with four openings as in Test Example 9, and the mixture was dissolved with stirring for 10 minutes. After a solution obtained by dissolving terephthaloyl dichloride 10.2 g (0.05 moles) in acetone 100 ml was dropped into this flask by means of the dropper funnel over one hour at room temperature, a slurry with solid component containing cyclic imino ester was obtained by iminoesterification for one hour with reflux. A solid component was separated from this slurry and after it was washed with water 300 ml and dried, a dried solid component 16.2 g (acid value 3.2) containing cyclic imino ester was obtained. The dried solid component 15 g and water 48 g were placed in the flask and 1% aqueous solution of sodium carbonate 4.54 g was added with stirring and an alkali treatment was effected at 30° C. for 30 minutes with stirring. The alkali-treated solid component was filtered out and washed with warm water 130 g at 60° C. After the washed solid component was dehydrated, it was dried for 2 hours with a hot-air drier at 100° C. to obtain yellowish powder 14.3 g. This yellowish powder was analyzed and found to contain cyclic imino ester by 99.92%. Its acid value was $9 \times 10^{-2}$ and its chlorine ion content was $3 \times 10^2$ ppm. This will be referred to as Absorbent (P-11).

TEST EXAMPLE 12

Anthranilic acid 13.7 g (0.1 moles), potassium hydroxide 5.32 g (0.095 moles) and water 100 ml were placed in a flask with four openings as in Test Example 9, and the mixture was dissolved with stirring for 10 minutes. After a solution obtained by dissolving terephthaloyl dichloride 10.2 g (0.05 moles) in acetone 200 ml was dropped into this flask by means of the dropper funnel over one hour at room temperature, a slurry with solid component containing N,N'-bis(o-carboxyphenylterephthalamid) was obtained by amidation for one hour with reflux. A solid component was separated from this slurry and after it was washed with water 300 ml and dried, a dried solid component 19.8 g was obtained. The dried solid component 19.8 g, acetic anhydride 102 g (1 mole) and toluene 100 ml were placed in the flask for iminoesterification with reflux for 4 hours, and after it was cooled down to room temperature, a solid component was filtered. After the filtered solid component was washed with acetone 100 ml, it was dried to obtain a solid component 15.6 g (acid value 5.1) containing cyclic imino ester was obtained. This dried solid component 15 g and water 35 g were placed in the flask and 1% aqueous solution of potassium hydroxide 7.65 g was added with stirring and an alkali treatment was effected at 25° C. for 30 minutes with stirring. The alkali-treated solid component was filtered out and washed with warm water 100 g at 60° C. After the washed solid component was dehydrated, it was dried for 2 hours with a hot-air drier at 100° C. to obtain yellowish powder 14.35 g. This yellowish powder was analyzed and found to contain cyclic imino ester by 99.71%. Its acid value was $8 \times 10^{-1}$ and its chlorine ion content was $9 \times 10^2$ ppm. This will be referred to as Absorbent (P-12).

COMPARISON EXAMPLE 5

Absorbent (P-9) obtained in Test Example 9 10 g and $1 \times 10^{-2}$% aqueous solution of sodium hydroxide 1000 ml were placed in a beaker. After it was stirred for one hour with a mixer, a solid component was filtered. The filtered solid component and water 1000 ml were placed in a beaker, and after it was stirred for one hour with a mixer, a solid component was filtered. This routine was repeated three times and the solid component thus obtained was dried for one hour at 100° C. to obtain yellowish powder. This yellowish powder was analyzed and found to contain cyclic imino ester by 100.00%. Its acid value was $6 \times 10^{-4}$ and its chlorine ion content was $5 \times 10^{-2}$ ppm. This will be referred to as Absorbent (R-5).

COMPARISON EXAMPLE 6

Yellowish powder 17.0 g was obtained in the same way as in Test Example 9 except that the alkali treatment was dispensed with. This yellowish powder was analyzed and found to contain cyclic imino ester by 99.20%. Its acid value was 1.4 and its chlorine ion content was $1.8 \times 10^3$ ppm. This will be referred to as Absorbent (R-6).

Part 4 (Evaluation on Ultraviolet Radiation Absorption)

Each of the ultraviolet radiation absorbents 1.0 mg prepared in Parts 1, 2 and 3 was dissolved in 200 ml of 1,1,2,2-tetrachlorethane of the optical grade and transparency at 350 nm measured by using a UV-Vis spectrophotometer (U2000 produced by Hitachi, Ltd.) was evaluated according to the following standard.
A: Transparency less than 25%
B: Transparency greater than 25% but less than 26%
C: Transparency greater than 26%

The results are shown in Table 1.

Part 5 (Evaluation of Shelf Life)

Ultraviolet radiation absorbents 10 g prepared in Parts 2 and 3 were each placed in a receptacle and stored for six months inside a humidity controllable incubator at temperature 40° C. and humidity 50%. The acid value was measured before and after the storage period and the increase was evaluated according to the following standard:
A: Increase in acid value less than $1 \times 10^{-2}$.
B: Increase in acid value greater than $1 \times 10^{-2}$ and less than $1 \times 10^{-1}$.
C: Increase in acid value greater than $1 \times 10^{-1}$ and less than 1.
D: Increase in acid value greater than 1.

Part 6 (Evaluation when Absorbents are Added and Mixed with Polyethylene Terephthalate)

Ultraviolet radiation absorbents prepared in Parts 1, 2 and 3 were evaluated regarding resistance against heat and transparency when added to and mixed with polyethylene terephthalate with intrinsic viscosity 0.70. Those prepared in Parts 1 and 3 were evaluated for workability in similar situations.

For evaluating resistance against heat, 100 parts of polyethylene terephthalate chips and 2 parts of each of the absorbents prepared in Parts 1–3 were subjected to a dry blending process and extruded while a double-axis extruder was used to mix them together at 280° C. After the mixture was cooled and made into pellets, they were dried in vacuum. The vacuum-dried pellets 10 g were put inside a test tube to prepare Samples B obtained by heating and melting for 10 minutes and Samples T obtained by heating and melting for 60 minutes. Both Samples B and T were checked visually and evaluated according to the following standard:
A: No difference between B and T and no abnormalities such as burns were observed on T.
B: T is somewhat more yellowish than B but no abnormalities such as burns were observed on T.
C: T is clearly more yellowish than B and burns were observed on parts of T.

For evaluating transparency, 100 parts of polyethylene terephthalate chips and 2 parts each of the absorbents prepared in Parts 1–3 were subjected to a dry blending process and extruded from a T-die while a double-axis extruder was used to mix them together at 280° C. and cooled by means of a cooling roller at about 50° C. to produce non-crystalline sheets of thickness about 1 mm. Blank sheets were separately prepared in the same manner except without blending the ultraviolet radiation absorbents. Evaluation of transparency was carried out according to the following standard:
A: As transparent as the blanks
B: Very little more cloudy than the blanks
C: A little more cloudy than the blanks
D: Definitely more cloudy than the blanks For the evaluation of workability, 100 parts of polyethylene terephthalate chips and 2 parts each of the absorbents prepared in Parts 1 and 3 were subjected to a dry blending process. Extrusion was repeated continuously for 6 hours while a double-axis extruder was used to mix them together at 280° C. Presence or absence of deposits at the vent opening of the extruder was visually checked one hour, 3 hours, and 6 hours after the starting of the extrusion and workability was evaluated according to the following standard:

A: Deposits not observed after 6 hours
B: Deposits not observed after 3 hours but observed after 6 hours
C: Deposits not observed after one hour but observed after 3 hours
D: Deposits observed after one hour Part 7 (Evaluation when Absorbents are Added and Mixed with Polycarbonate)

Ultraviolet radiation absorbents prepared in Parts 1, 2 and 3 were evaluated regarding resistance against heat and transparency when added to and mixed with polycarbonate chips (Panlite, produced by Teijin Chemicals, Ltd). Those prepared in Parts 1 and 3 were evaluated for workability in similar situations.

For evaluating resistance against heat, 100 parts of polycarbonate chips and 2 parts each of the absorbents prepared in Parts 1–3 were subjected to a dry blending process and a double-axis extruder was used to mix them together at 290° C. After the extrusion, it was cooled with water, made into pellets and dried in vacuum for 5 hours at 100° C. Evaluations were made as in Part 6.

For evaluating transparency, 100 parts of polycarbonate chips and 2 parts each of the absorbents prepared in Parts 1–3 were subjected to a dry blending process and a double-axis extruder was used to mix them together at 290° C. and they were extruded from a T-die and cooled by means of a cooling roller at about 50° C. to produce sheets of thickness about 1 mm. Evaluations were made as in Part 6.

For evaluating workability, 100 parts of polycarbonate chips and 2 parts each of the absorbents prepared in Parts 1 and 3 were subjected to a dry blending process. Extrusion was repeated continuously for 6 hours while a double-axis extruder was used to mix them together at 290° C. Evaluations were made as in Part 6.

TABLE 1

| | Absorbent | | | Evaluations | | | | | | | |
|---|---|---|---|---|---|---|---|---|---|---|---|
| | Kind/Con-centration (%) | Acid value | Chlorine ion content (ppm) | | | PET | | | PC | | |
| | | | | AB | SL | RH | WK | TR | RH | WK | TR |
| Test | | | | | | | | | | | |
| 1 | P-1/99.99 | $1.5 \times 10^{-3}$ | — | A | — | B | B | A | B | B | B |
| 2 | P-2/99.99 | $4 \times 10^{-3}$ | — | A | — | B | A | A | B | B | A |
| 3 | P-3/99.95 | $8 \times 10^{-2}$ | — | A | — | B | A | A | B | A | A |
| 4 | P-4/99.65 | $9 \times 10^{-1}$ | — | B | — | B | A | B | B | A | B |
| Comp | | | | | | | | | | | |
| 1 | R-1/100.00 | $6 \times 10^{-4}$ | — | A | — | B | D | D | B | D | D |
| 2 | R-2/99.41 | 1.3 | — | C | — | D | A | D | D | A | D |
| Test | | | | | | | | | | | |
| 5 | P-5/99.99 | — | $1.5 \times 10^{-1}$ | A | B | B | — | A | B | — | A |
| 6 | P-6/99.99 | — | $2 \times 10^{-1}$ | A | B | B | — | A | B | — | A |
| 7 | P-7/99.90 | — | $4 \times 10^{2}$ | A | A | B | — | A | B | — | A |
| 8 | P-8/99.94 | — | $9.5 \times 10^{2}$ | B | A | B | — | B | B | — | B |
| Comp | | | | | | | | | | | |
| 3 | R-3/100.00 | — | $5 \times 10^{-2}$ | A | D | B | — | D | B | — | D |
| 4 | R-4/98.79 | — | $2 \times 10^{3}$ | C | A | D | — | D | D | — | D |
| Test | | | | | | | | | | | |
| 9 | P-9/99.96 | $3 \times 10^{-3}$ | $1.5 \times 10^{-1}$ | A | B | B | A | B | B | A | B |
| 10 | P-10/99.94 | $5 \times 10^{-3}$ | $3 \times 10^{-1}$ | A | B | B | A | A | B | A | A |
| 11 | P-11/99.92 | $9 \times 10^{-2}$ | $3 \times 10^{2}$ | A | A | B | B | A | B | B | A |
| 12 | P-12/99.71 | $8 \times 10^{-1}$ | $9 \times 10^{2}$ | B | A | B | B | B | B | B | B |
| Comp | | | | | | | | | | | |
| 5 | R-5/100.00 | $6 \times 10^{-4}$ | $5 \times 10^{-2}$ | A | D | B | D | D | B | D | D |
| 6 | R-6/99.20 | 1.4 | $1.8 \times 10^{3}$ | C | A | D | A | D | D | A | D |

In Table 1:
Test: Test Example
Comp: Comparison Example
Concentration: Concentration (%) of cyclic imino ester in ultraviolet radiation absorbent for thermoplastic polymers
PET: Polyethylene terephthalate
PC: Polycarbonate
AB: Absorbence of ultraviolet radiation
SL: Shelf life
RH: Resistance against heat
WK: Workability
TR: Transparency As can be understood from above, each of the absorbents of Test Examples 1–12 satisfies the requirements on the ability to absorb ultraviolet radiation, resistance against heat and transparency and each of the absorbents of Test Examples 1–4 and 9–12 also satisfy the requirement on workability. Each of the absorbents of Test Examples 5–12 also has a good shelf life. In particular, those of Test Examples 9–11 with concentration of cyclic imino ester greater than 99.9% and less than 100%, having an acid value in the range of $3 \times 10^{-3}$–$1 \times 10^{-1}$ and a chlorine ion content within the range of $1.5 \times 10^{-1}$–$5 \times 10^{2}$ ppm are excellent. By contrast, Comparison Examples 1, 3 and 5 are substantially purely cyclic imino ester without hardly any acidic substance which affects the acid value or any chlorine ion, being not good in transparency and poor in either workability or shelf life. Comparison Examples 2, 4 and 6 contain relatively large quantities of acidic substance and chlorine ions and the content of cyclic imino ester is accordingly lower. They are inferior in the ability to absorb ultraviolet radiation and also poor in resistance against heat and transparency.

In summary, the absorbents according to this invention are themselves superior in resistance against heat and capable of being added to and mixed with thermoplastic polymers such as polyethylene terephthalate or polycarbonate to obtain molded products with the same transparent characteristic of the thermoplastic polymers, not adversely affecting the environmental conditions during the mixing and molding processes and themselves having a good shelf life.

What is claimed is:

1. A method of producing an ultraviolet radiation absorbent composition for thermoplastic polymers, said method comprising Step a and Step b;

said Step a being a process of iminoesterification of isatoic anhydride and terephthaloyl dichloride in presence of a solvent and an alkali, followed by separating from the reaction mixture a cyclic iminoester compound solid component shown by Formula 1 given below

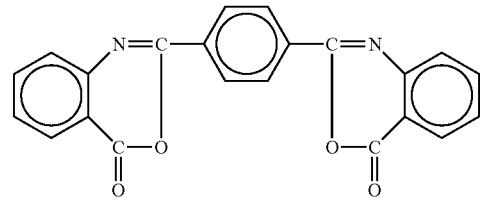

Formula 1 said Step b being a process of treating the solid component separated in said Step a with an alkaline solution and further washing with water to obtain the ultraviolet radiation absorbent composition for thermoplastic polymers containing cyclic imino ester compound shown by Formula 1 in an amount of over 99.5 weight % and less than 100 weight % and having an acid value in the range of $1 \times 10^{-3}$–1 KOHmg/g and a chlorine ion content in the range of $1 \times 10^{-1}$–$1 \times 10^{-3}$ ppm.

2. The method of claim 1 wherein said Step b the ultraviolet radiation absorbent for thermoplastic polymers is obtained containing cyclic imino ester compound shown by Formula 1 in an amount of over 99.9 weight % and less than 100 weight % and having an acid value in the range of $3 \times 10^{-3}$–$1 \times 10^{-1}$ KOHmg/g and a chlorine ion content in the range of $1.5 \times 10^{-1}$–$5 \times 10^{2}$ ppm.

* * * * *